United States Patent [19]

Hakim et al.

[11] 4,387,715
[45] Jun. 14, 1983

[54] SHUNT VALVE

[75] Inventors: Salomon Hakim, Bogota, Colombia; Carlos A. Hakim, Fort Lauderdale, Fla.

[73] Assignee: Hakim Company Limited, Saint Vincent, British West Indies

[21] Appl. No.: 372,813

[22] Filed: Apr. 28, 1982

Related U.S. Application Data

[63] Continuation-in-part of Ser. No. 190,018, Sep. 23, 1980, Pat. No. 4,332,255, which is a continuation-in-part of Ser. No. 2,354, Jan. 10, 1979, abandoned.

[51] Int. Cl.³ ............................................. A61M 27/00
[52] U.S. Cl. ......................................................... 604/9
[58] Field of Search .................... 128/350 V; 137/539

[56] References Cited

U.S. PATENT DOCUMENTS 4,332,255  6/1982  Hakim et al. .................. 128/350 V Primary Examiner—C. Fred Rosenbaum
Attorney, Agent, or Firm—Kenway & Jenney

[57] ABSTRACT

In a surgically implantable shunt system for venting cerebrospinal fluid in the treatment of hydrocephaly, a valve and the method of testing it are disclosed. The valve comprises an elongate hollow valve body into which a flat plate tightly fits, partitioning the valve body into an outlet and an inlet chamber. The flat plate has a circular aperture connecting the chambers and upon which rests a spherical ball of diameter larger than the aperture. A flat spring biases the ball against the circular periphery of the aperture creating a circular seal and providing a precisely defined back pressure, low hysteresis and low susceptibility to bridging by debris. Testing for leakage is accomplished by illuminating with light of a suitable frequency the aperture with ball seated and detecting any light transmitted therethrough.

9 Claims, 15 Drawing Figures

SHUNT VALVE

BACKGROUND OF THE INVENTION

This is a continuation-in-part of U.S. Serial No. 190,018, filed Sept. 23, 1980, now U.S. Pat. No. 4,332,255, entitled "Shunt Valve" which is a continuation-in-part of U.S. Ser. No. 2,354, filed Jan. 10, 1979, entitled "Shunt Valve" and now abandoned.

This invention relates to a valve in a surgically implantable shunt system for venting cerebrospinal fluid (CSF) from a cerebroventricular catheter to a drainage catheter and more particularly to such a valve for presenting a precisely controllable and adjustable back pressure to the cerebral ventricles in case of hydrocephaly and similar conditions of impaired circulation and absorption of cerebrospinal fluid.

Mechanical devices for controlling the drainage of cerebrospinal fluid into the bloodstream are in use, an example of which is the shunt device of U.S. Pat. No. 3,288,142. These devices include valves such that the flow is unidirectional from the ventricles to drainage into the circulatory system. While quite successful, such valves are relatively expensive and difficult to fabricate. These prior valves are also somewhat heavy and bulky, their metal parts interferring, for example, with X-ray scanning procedures. Previously known devices also sometimes become clogged with brain debris or with CSF protein when elevated to abnormally high levels. This is particularly true of so-called slit valves which have been used for this purpose, e.g., valves which are merely a thin slit in a silastic tube. Such debris can prevent the valve from sealing properly, thereby degrading its ability to regulate closely the back pressure presented to the cerebral ventricles. Wide hysteresis between opening and closing pressures has been another shortcoming of known shunt valves for use in treating hydrocephaly, i.e., there has not been a well defined "popping" pressure at which pressure the valve opens. Establishing the desired pressure in known valves has been another area of difficulty.

Testing of known valves has been accomplished previously by subjecting the valves to a vacuum or a gas pressure, or even exposure to a liquid environment. These methods are cumbersome, time consuming and often foul the valve in the testing process.

An object of this invention, therefore, is to develop a simple, highly reliable cerebroventricular shunt valve which is compact, light in weight, minimally opaque to X-rays, and inexpensive to manufacture.

Another object is to produce a shunt valve having low hysteresis and low susceptibility to clogging with debris, enabling it to present a precisely controllable back pressure to the cerebral ventricles.

Yet another object is a shunt valve which allows its operating pressure to be set very accurately.

Still another object is a shunt valve whose operating pressure may be continuously adjusted.

A still further object is to develop a method of testing the sealing effectiveness of such a valve during manufacture by simple optical means.

Yet another object of this invention is a shunt valve whose operating pressure is readily adjustable at the time of implantation and which is consistent and repeatable.

A still further object is a shunt valve whose operating pressure is substantially insensitive to changes in viscosity of the cerebro-spinal fluid.

Other objects, features and advantages of the present invention will become apparent in what follows.

SUMMARY OF THE INVENTION

According to the present invention, a valve for precisely controlling the back pressure presented to the cerebral ventricles in a hydrocephalus shunt device has an elongate, hollow valve body internally partitioned so as to form an inlet chamber and an outlet chamber. The inlet chamber is coupled to a ventricular catheter; the outlet chamber is coupled to a drainage catheter. The valve is designed for use in a hydrocephalus treatment system, for example, as shown in FIG. 1 of applicant's U.S. Pat. No. 3,527,226. The internal partitioning is accomplished by means of a thin, flat plate tightly fitting within the tubular valve body. This plate is provided with a circular aperture connecting the inlet and outlet chambers. A spherical ball of diameter larger than that of the aperture in the thin plate serves to restrict the flow through the aperture in a controlled manner. A spring, including a cantilevered flat portion overlying the ball and touching it at a single point biases it against the circular periphery of the flat plate aperture, effecting, when the valve is closed, a circular seal between the ball and aperture. This arrangement provides a precisely defined back pressure with low hysteresis and low susceptibility to clogging by debris. In a preferred embodiment the flat plate has a struck up rear portion which presses against the spring for adjusting the back pressure of the valve. In another embodiment, a screw threadably supported by the valve body, presses against the cantilevered portion of the spring permitting the back pressure of the valve to be accurately adjusted.

In yet another embodiment of the invention disclosed herein, the spring includes a central portion extending from a rear end of the spring and adapted for overlying the ball, and a pair of arms flanking the central portion and extending from the rear end of the spring. The ends of these arms are attached to the flat plate. A screw supported by the flat plate is positioned for engaging the rear end of the spring so that the opening pressure of the valve can be accurately adjusted. In this embodiment the flanking arms may be splayed apart and also extend beyond the central portion of the spring. In still another embodiment, the spring comprises a first spring portion overlying the ball and a second portion having a first and a second end. The second end is attached to the flat plate and the first spring portion is attached to the second spring portion near its second end. A screw supported in the flat plate is adapted to engage the first end of the second spring portion so that the opening pressure of the valve can be adjusted. Alternatively, the valve includes a spring having a first portion overlying the ball and a second portion which includes a semicircular bend. The lower portion of the second portion is affixed to the flat plate and the first portion of the spring attached to the upper surface of the second portion. In addition, a screw is provided to engage the second portion for adjusting the opening pressure of the valve.

The effectiveness of the valve seal is tested during manufacture by optical means. Light energy at a wavelength for which the ball is opaque is directed upon the aperture with ball in place. Absence of light leakage indicates a properly sealing valve.

BRIEF DESCRIPTION OF THE DRAWING

The present invention will be better understood by reference to the following drawing in which.

Corresponding reference characters indicate corresponding parts throughout the several views of the drawings.

DESCRIPTION OF THE PREFERRED EMBODIMENT

Figure 1:
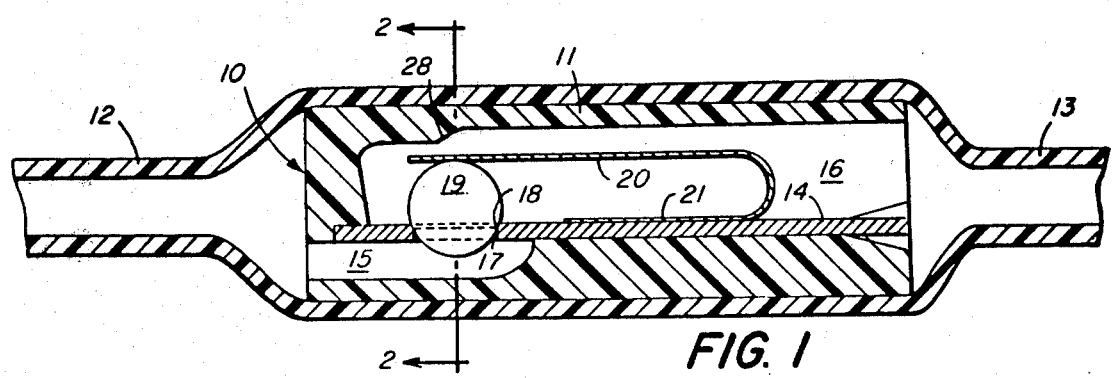
FIG. 1 is a longitudinal sectional view of the valve device.
Figure 3:
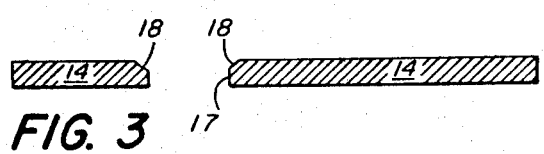
FIG. 3 is an edge view of the flat plate portion of the valve device.
Figure 2:
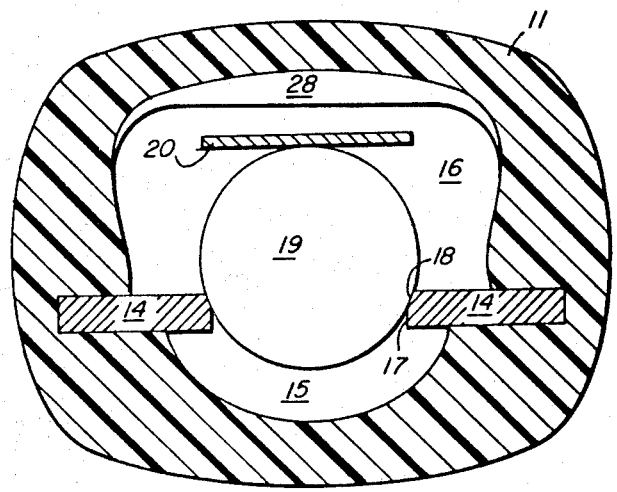
FIG. 2 is a sectional view of the valve device along section lines 2—2 of FIG. 1.

Referring to FIGS. 1 and 2, the valve device 10 comprises a hollow valve body 11, preferably made of injection molded polyethersulfone plastic. Valve body 11 couples at its inlet end to cerebroventricular catheter 12, and its outlet end with a drainage catheter 13 or with a pumping system, including a second valve, i.e., in the manner shown in U.S. Pat. No. 3,527,226. Tightly fitting within valve body 11 is a thin, flat plate 14, preferably made of stainless steel, which partitions the valve body 11 into an inlet chamber 15 and an outlet chamber 16. In this embodiment, the thin plate 14 is 0.38 inch long, 0.14 inch wide and 0.01 inch thick. A highly polished circular aperture 17 of diameter 0.057 inch is cut through flat plate 14 thereby connecting inlet chamber 15 and outlet chamber 16 providing a flow path for cerebrospinal fluid from the cerebral ventricles to drainage into the circulatory system. As can be seen more clearly in FIG. 3, circular aperture 17 in flat plate 14 has a coined rim 18, the radius of curvature of which matches the radius of spherical ball 19, thereby providing a seat for the ball 19. In this embodiment, the radius of curvature of rim 18 is approximately 0.620 inch. The combination of valve body 11 and thin plate 14 allows this shunt valve to be light in weight, compact and inexpensive to manufacture.

Spherical ball 19 for controllably restricting flow through the valve is a highly polished hard material, preferably ruby or synthetic sapphire, having a diameter of 0.620 inch which is larger than the diameter of aperture 17 so that it rests against coined rim 18 of aperture 17 without passing through, thereby forming a seal. The highly polished surfaces of ball 19 and aperture 17 ensure an effective seal when ball 19 is seated, and furthermore, lessen any tendency for the ball to become stuck in the seated position, so enabling a precisely defined and repeatable operating pressure.

Figure 4:
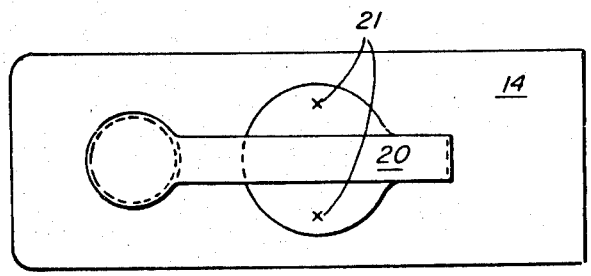
FIG. 4 is a plan view of the flat plate portion of the valve device.

Referring now to FIG. 1 and FIG. 4, flat spring 20, having a semicircular bend, is attached to flat plate 14 at 21 by spot welding or other suitable means. The constant of the spring 20 may be varied by altering its width or thickness, thereby allowing for valves with different operating pressures. Spring 20, parallel to the plane of aperture 17, overlies ball 19, touching it at essentially a single point and biasing it against rim 18 of aperture 17. This arrangement achieves a narrow hysteresis between opening and closing pressures. When the valve is open, ball 19 is able to spin freely because of the point contact with spring 20, discouraging the accumulation of debris and permitting close regulation of the back pressure presented to the lateral ventricles.

Valve 10 is assembled by inserting the flat plate-ball-spring assembly into valve body 11 from the right side of FIG. 1. The contour of chamber 16 is such that ball 19 will remain within aperture 17 after assembly. That is, shoulder 28 limits the extension of spring 20, thereby assuring that ball 19 cannot become dislodged from aperture 17.

Figure 5:
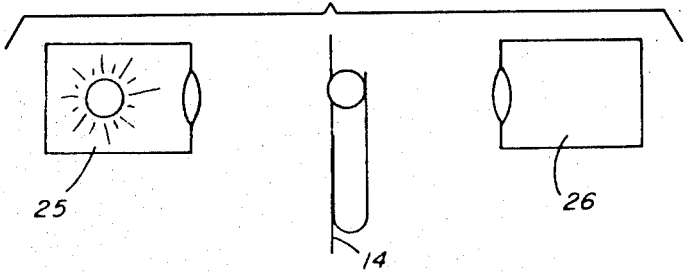
FIG. 5 is a schematic representation of the optical method for testing the sealing effectiveness of the valve device.

In FIG. 5, the method of testing the sealing characteristics of the shunt valve disclosed herein is illustrated. Light source 25 illuminates one side of flat plate 14 with the ball 19 seated. The wavelength of the light from source 25 is selected so that ball 18 is opaque. With a sapphire ball, for example, green light is appropriate. A light detector 26 is arranged on the opposite side of flat plate 14 to detect any light which passes through aperture 17 of flat plate 14. Absence of light reaching the detector indicates a properly sealing valve.

Figure 6:
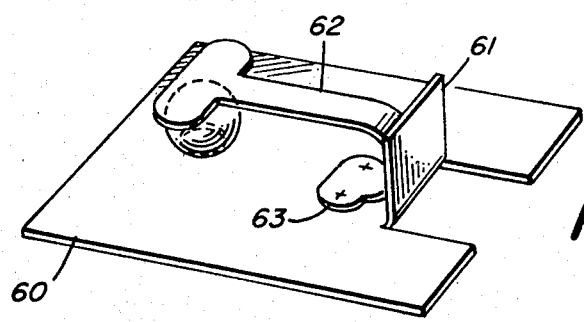
FIG. 6 is a perspective view of another embodiment of this invention.

In addition to adjusting back pressure by selecting the width or thickness of the ball-biasing spring, fine adjustments can be achieved with the embodiment of the invention shown in FIG. 6. In FIG. 6, a flat plate 60 has a struck up rear portion 61 which presses against the semicircular bend in a spring 62. To establish a desired value of back pressure, the spring 62 is first attached to flat plate 60 at 63 by spot welding or other suitable means. The struck up portion 61 is then forced (by means of a conventionl tool not shown) beyond its elastic limit so as to take a set against the spring 62. The spring constant of the spring 62 is thereby altered depending on the degree to which the struck up portion 61 is deformed to press against the semicircular bend in the spring 62. Thus, by adjusting the level of force with which the struck up portion 61 engages the spring 62, the operating back pressure of a valve incorporating the elements depicted in FIG. 6 may be very precisely set. An alternative way of accurately establishing a desired back pressure will now be described, still with reference to FIG. 6. Instead of first attaching the spring 62 to the flat plate 60, the struck up portion 61 is put into place, for example, oriented perpendicularly to the flat plate 60. The semicircular bend of spring 62 is then forced against the struck up portion 61 while the spring's operating pressure is continuously measured by conventional means. When the desired operating back pressure is attained, the spring 62 is then secured to the flat plate 60, as by spot welding at 63. The use of a struck up portion of the flat plate to adjust operating pressure is superior to attempting to alter operating pressure by deforming the spring 62 itself. This is the case because the thin spring material, having a large elastic limit, is difficult to deform with precision so as to achieve a desired operating pressure.

Figure 7:
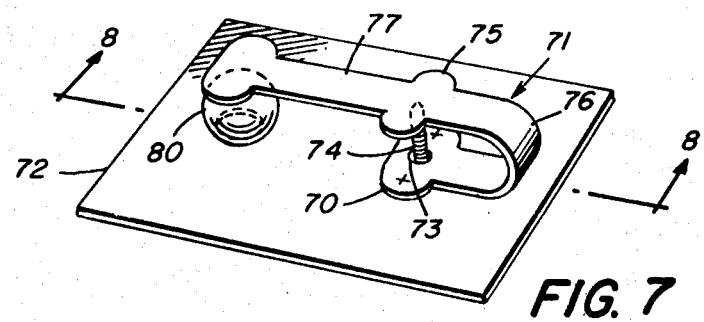
FIG. 7 is a perspective view of yet another embodiment.
Figure 8:
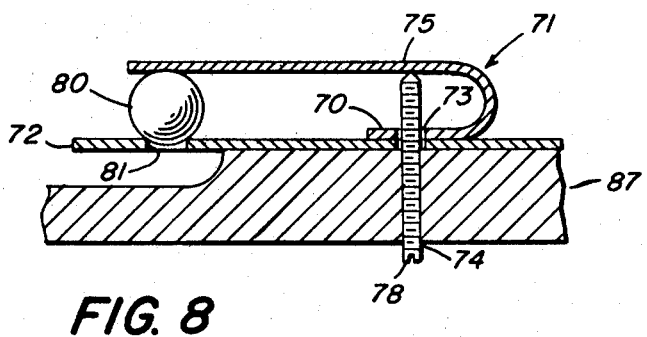
FIG. 8 is a sectional view along section lines 8—8 of FIG. 7.

Yet another embodiment of the invention allowing for accurate setting of the operating back pressure is shown in FIGS. 7 and 8. A base portion 70 of a spring 71 is attached, as by spot welding, to a flat plate 72. The base portion 70 has a hole 73 through which passes a screw 74. The screw 74 rests against an enlarged section 75 of the spring 71. The spring 71 also includes a wider, relatively stiff part 76 and a narrower section 77 which overlies a ball 80. As can be seen in FIG. 8, the screw 74 is threadably supported in a valve body 87 so that by inserting a tool (not shown) into a slot 78, the screw 74 may be rotated to adjust the degree to which it presses on the enlarged section 75 of the spring 71. In this way, the "popping" pressure of the ball 80 in an aperture 81 may be very accurately adjusted. In this embodiment, the operating pressure can be varied as desired during the operating lifetime of the valve.

Figure 9:
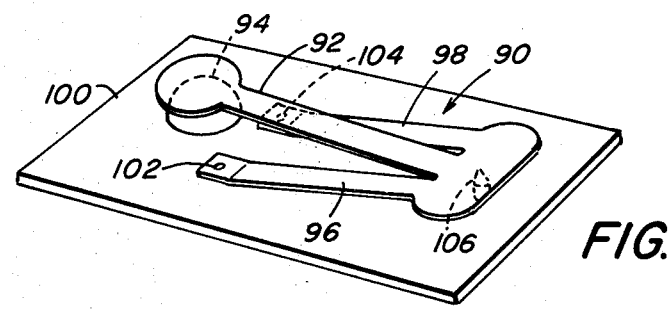
FIG. 9 is a perspective view of yet another embodiment of the invention disclosed herein.
Figure 10:
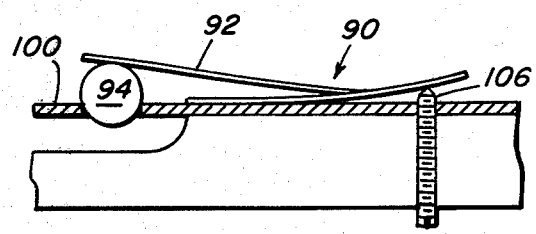
FIG. 10 is a side view of the embodiment of FIG. 9.
Figure 11:
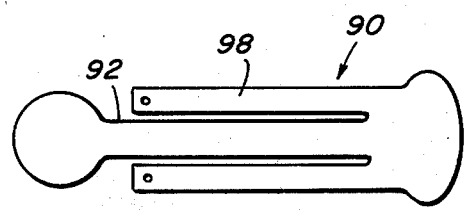
FIG. 11 is a plan view of the spring assembly of FIGS. 9 and 10.

Still another embodiment of the invention is illustrated in FIGS. 9, 10 and 11. A spring assembly 90 includes a central portion 92 which overlies a ball 94 shown in phantom. Flanking either side of the central portion 92 are arms 96 and 98 which are attached to a flat plate 100 by spot welding or other suitable means at locations 102 and 104. It is preferred that the spring assembly 90 be made from a single piece of material such as stainless steel. It is also preferred that the central portion and the flanking arms be created by photo-etching rather than some other process such as stamping. By means of a photo-etching process no strains are introduced into the spring material in the process of creating the central portion and flanking arms. In this way the repeatability of the opening pressure of the shunt valve is assured. As can be seen clearly in FIG. 10 a screw 106 is provided in flat plate 100 to engage the rear portion of the spring assembly 90. As the screw 106 is rotated, the rear portion of the spring assembly 90 moves up or down. In this way the opening pressure of the valve can be adjusted very accurately because changes in the elevation of the rear portion of the spring assembly 90 effect very small changes in the opening pressure. By this arrangement, relatively large motions of the screw 106 cause small variations in opening pressure so that its value can be set as desired.

Figure 12:
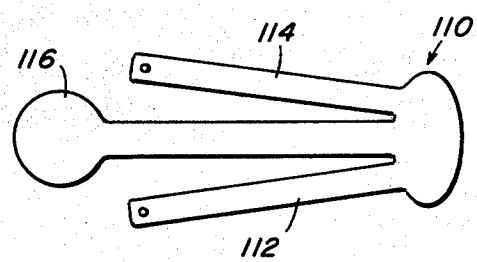
FIG. 12 is a plan view of another embodiment of the spring assembly adapted for use with the embodiments of FIGS. 9 and 10.
Figure 13:
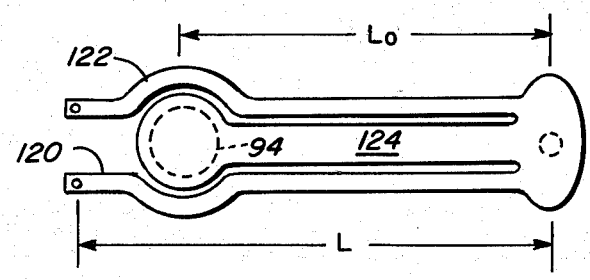
FIG. 13 is a plan view of yet another embodiment of the spring assembly disclosed herein.

FIG. 12 illustrates another embodiment of a spring assembly adapted for use with a shunt valve as disclosed herein. In this embodiment a spring assembly 110 includes flanking arms 112 and 114 which are splayed apart from a central member 116. By this arrangement a stiffer spring assembly is created. FIG. 13 shows another important embodiment of the invention herein. In this embodiment flanking arms 120 and 122 extend beyond the central portion 124. It is preferred that the length $L_O$ of the central portion 124 be approximately two-thirds the length L of the flanking arms 120 and 122. With such a geometrical relationship, as a screw such as 106 in FIG. 10 is moved up and down, the portion of the central member 124 which overlies the ball will simply rotate, there being no tendancy for this portion to translate across the top of the ball 94. In this way the opening pressure of the valve is highly repeatable since there will be substantially no forces other than those pushing the ball downward towards its seat.

For the embodiments of FIGS. 9–13, an approximate relationship has been derived relating the forces on the ball to the force produced by the screw acting on the rear of the spring assembly. For a homogeneous spring this relationship is $$Z = \frac{WL^3}{3EI} - \frac{L_0 WL^2}{2EI}.$$

In this equation, Z is the force biasing the ball into its seat, W is the upward force on the rear of the spring assembly due to the adjustable screw, L and $L_O$ are as described with reference to FIG. 13, E is Young's modulus of the spring, and I is the cross-sectional moment of inertia of the spring.

Figure 14:
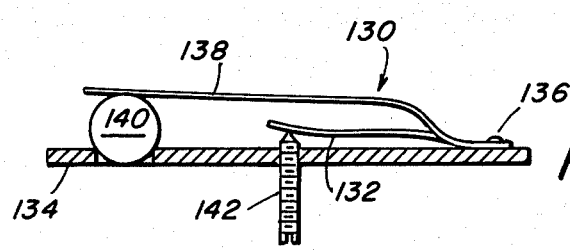
FIG. 14 is a side view of yet another embodiment of the spring assembly of this invention.
Figure 15:
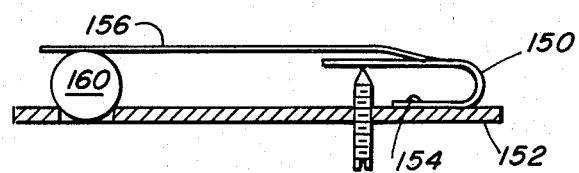
FIG. 15 is a side view of another embodiment of the spring assembly disclosed herein.

Other embodiments of the invention disclosed herein are found in FIGS. 14 and 15. In FIG. 14 a spring assembly 130 includes a first portion 132 which is affixed as by spot welding to a flat plate 134 at the location 136. Attached to the portion 132 is a spring portion 138 which overlies a ball 140. A screw 142 is adapted for passing through the flat plate 134 and engaging the spring member 132 at its front end. As is apparent, as the screw 142 moves up and down, the force which the portion 138 applies to the ball 140 is varied. Similarly, in FIG. 15 a first spring portion 150 is semicircular in shape and attached to a flat plate 152 at the location designated 154. A second spring portion 156 is attached to the upper portion of the member 150. A screw 158 is adapted for engaging the front portion of the spring portion 150 so as to adjust the force that the spring portion 156 applies to a ball 160. In both of the embodiments illustrated in FIG. 14 and FIG. 15 the sensitivity of opening pressure to screw position is reduced by the geometrical arrangements so that opening pressures can be set very precisely.

The embodiments illustrated in FIGS. 9–15 thus enable the opening pressure of the shunt valve to be adjusted very accurately. Because in these embodiments sensitivity of opening pressure to screw location is reduced by the spring arrangements, accurate settings can be made just before the shunt valve is installed by the surgeon. This arrangement may also allow changes in opening pressure to be effected after the shunt valve has been installed.

Although in these embodiments, injection molded polyethersulfone plastic has been used for valve body 11 and stainless steel for flat plate 14 and spring 19, it is obvious that other stable, essentially inert and non-toxic materials could be utilized. Similarly, although ruby is the preferred material for ball 19, other hard, non-toxic and inert materials such as synthetic sapphire could be substituted.

The dissolved valve is, therefore, compact, light in weight, inexpensive to manufacture and simple to assemble. More importantly, the valve achieves a tight regulation of the cerebrospinal fluid pressure within the cerebral venticles.

While the above describes and illustrates a preferred embodiment of the invention, it is to be understood that the invention is not so limited, but covers all modifications which should be apparent to one skilled in the art and falling within the scope of the invention.

What is claimed is:

1. In a surgically implantable shunt system in which cerebrospinal fluid is vented from a cerebroventricular catheter to a drainage catheter, a valve for presenting a precisely controllable back pressure to the ventricles, said valve comprising:
   an elongate, hollow valve body;
   a flat plate partitioning said valve body so as to form an inlet chamber and an outlet chamber, said ventricular catheter being coupled to said inlet chamber and said drainage catheter being coupled to said outlet chamber, said plate being provided with a circular aperture connecting said inlet and outlet chambers;
   a spherical ball of diameter larger than said aperture for controllably restricting flow through said aperture;
   a spring including a cantilevered flat portion overlying said ball and biasing it against the circular periphery of said aperture whereby a circular seal is selectively effected between said ball and said plate, providing a precisely defined back pressure with low hysteresis and low susceptibility to bridging by debris;
   wherein said spring comprises a central portion extending from a rear end thereof and adapted for overlying said ball and a pair of arms flanking said central portion and extending from said rear end, the ends of said arms adapted for attachment to said flat plate.

2. The valve of claim 1 wherein said flanking arms are splayed apart.

3. The valve of claim 1 wherein said flanking arms extend beyond said central portion.

4. The valve of claim 1, claim 2 or claim 3 further including screw means supported by said flat plate and adapted for engaging said rear end of said spring whereby the opening pressure of said valve can be accurately adjusted.

5. The valve of claim 1 wherein said central portion is approximately two-thirds of the length of the flanking arms.

6. In a surgically implantable shunt system in which cerebrospinal fluid is vented from a cerebroventricular catheter to a drainage catheter, a valve for presenting a precisely controllable back pressure to the ventricles, said valve comprising:
   an elongate, hollow valve body;
   a flat plate partitioning said valve body so as to form an inlet chamber and an outlet chamber, said ventricular catheter being coupled to said inlet chamber and said drainage catheter being coupled to said outlet chamber, said plate being provided with a circular aperture connecting said inlet and outlet chambers;
   a spherical ball of diameter larger than said aperture for controllably restricting flow through said aperture;
   a spring including a cantilevered flat portion overlying said ball and biasing it against the circular periphery of said aperture whereby a circular seal is selectively effected between said ball and said plate, providing a precisely defined back pressure with low hysteresis and low susceptibility to bridging by debris;
   wherein said spring comprises a first portion overlying said ball and a second portion having a first and a second end, said second end adapted for attachment to said flat plate, wherein said first spring portion is attached to said second spring portion near said second end, and screw means supported in said flat plate and adapted for engaging said first end of said second spring portion whereby the opening pressures of said valve can be adjusted.

7. In a surgically implantable shunt system in which cerebrospinal fluid is vented from a cerebroventricular catheter to a drainage catheter, a valve for presenting a precisely controllable back pressure to the ventricles, said valve comprising:
   an elongate, hollow valve body;
   a flat plate partitioning said valve body so as to form an inlet chamber and an outlet chamber, said ventricular catheter being coupled to said inlet chamber and said drainage catheter being coupled to said outlet chamber, said plate being provided with a circular aperture connecting said inlet and outlet chambers;
   a spherical ball of diameter larger than said aperture for controllably restricting flow through said aperture;
   a spring including a cantilevered flat portion overlying said ball and biasing it against the circular periphery of said aperture whereby a circular seal is selectively effected between said ball and said plate, providing a precisely defined back pressure with low hysteresis and low susceptibility to bridging by debris;
   wherein said spring comprises a first portion overlying said ball and a second portion including a semicircular bend, the lower portion of said second portion affixed to said flat plate and said first portion of said spring attached to the upper surface of said second portion, and screw means supported by said flat plate adapted to engage said second portion for adjusting the opening pressure of said valve.

8. In a surgically implantable shunt system in which cerebrospinal fluid is vented from a cerebroventricular catheter to a drainage catheter, a valve for presenting a precisely controllable back pressure to the ventricles, said valve comprising:
   an elongate, hollow valve body;
   a flat plate partitioning said valve body so as to form an inlet chamber and an outlet chamber, said ventricular catheter being coupled to said inlet chamber and said drainage catheter being coupled to said outlet chamber, said plate being provided with a circular aperture connecting said inlet and outlet chambers;
   a spherical ball of diameter larger than said aperture for controllably restricting flow through said aperture; and
   a spring assembly overlying said ball and biasing it against the circular periphery of said aperture whereby a circular seal is selectively effected between said ball and said plate, said spring assembly comprising a central portion extending from a rear end thereof and adapted for overlying said ball and a pair of arms flanking said central portion and extending from said rear end, the ends of said arms adapted for attachment to said flat plate, and screw means supported by said flat plate and adapted for engaging said rear end of said spring assembly whereby the opening pressure of said valve can be accurately adjusted.

9. In a surgically implantable shunt valve including a ball biased against a hole in a flat plate to effect a seal, means for biasing said ball against said flat plate comprising:
a first spring means having one end affixed to said flat plate;
a second spring means affixed to the other end of said first spring means and adapted for overlying said ball; and
means for adjusting the biasing force comprising screw means threadably supported by said flat plate and adapted for engaging said other end of said first spring means;
the compliances of said first and second spring means and their respective lengths selected to provide low sensitivity of change in said bias force with the position of said screw means.

* * * * *